US012320809B2

(12) United States Patent
Higuchi et al.

(10) Patent No.: US 12,320,809 B2
(45) Date of Patent: Jun. 3, 2025

(54) METHOD FOR MEASURING VIRAL ANTIGEN IN SAMPLE, ANTIBODY SET, AND REAGENT KIT

(71) Applicant: SYSMEX CORPORATION, Kobe (JP)

(72) Inventors: Keiko Higuchi, Kobe (JP); Naoki Nishiyama, Kobe (JP); Megumi Goto, Kobe (JP); Nobuyuki Ide, Kobe (JP)

(73) Assignee: SYSMEX CORPORATION, Kobe (JP)

(*) Notice: Subject to any disclaimer, the term of this patent is extended or adjusted under 35 U.S.C. 154(b) by 905 days.

(21) Appl. No.: 17/387,409

(22) Filed: Jul. 28, 2021

(65) Prior Publication Data
US 2022/0034883 A1 Feb. 3, 2022

(30) Foreign Application Priority Data

Jul. 29, 2020 (JP) ................. 2020-128480

(51) Int. Cl.
G01N 33/569 (2006.01)
G01N 33/543 (2006.01)
G01N 33/563 (2006.01)

(52) U.S. Cl.
CPC . *G01N 33/56983* (2013.01); *G01N 33/54326* (2013.01); *G01N 33/563* (2013.01)

(58) Field of Classification Search
CPC ....... G01N 33/56983; G01N 33/54326; G01N 33/563
See application file for complete search history.

(56) References Cited

U.S. PATENT DOCUMENTS

| | | | | |
|---|---|---|---|---|
| 2008/0160508 A1* | 7/2008 | Imoarai | ............ | G01N 33/54388 435/5 |
| 2008/0254440 A1* | 10/2008 | Uchida | ............ | G01N 33/56983 435/339 |
| 2009/0087869 A1* | 4/2009 | Fujimoto | ................ | G01N 33/76 436/500 |
| 2009/0087926 A1* | 4/2009 | Hasegawa | ........ | G01N 33/54388 436/518 |
| 2009/0111091 A1 | 4/2009 | Fujimoto et al. | | |
| 2009/0246861 A1* | 10/2009 | Manabe | ........... | G01N 33/54386 435/287.8 |
| 2009/0280507 A1 | 11/2009 | Fujimoto et al. | | |
| 2015/0072889 A1 | 3/2015 | Lui et al. | | |
| 2022/0056112 A1* | 2/2022 | Wu | ........................ | C07K 19/00 |
| 2022/0128560 A1* | 4/2022 | Hosimer | .......... | G01N 33/56983 |
| 2023/0296601 A1* | 9/2023 | Liu | ........................ | G01N 21/76 435/5 |
| 2023/0391855 A1* | 12/2023 | Saphire | .............. | G01N 33/6854 |

FOREIGN PATENT DOCUMENTS

| | | |
|---|---|---|
| CN | 103201289 A | 7/2013 |
| CN | 111153991 A | 5/2020 |
| CN | 111239391 A | 6/2020 |
| CN | 111303254 A | 6/2020 |
| CN | 111303280 A | 6/2020 |
| CN | 111398583 A * | 7/2020 ....... G01N 33/56983 |
| CN | 111398589 A | 7/2020 |
| CN | 111423508 A | 7/2020 |
| CN | 111704666 A * | 9/2020 ............. C07K 16/10 |
| WO | 2007/043582 A1 | 4/2007 |

OTHER PUBLICATIONS

Gibbs, R.A. et al. (2004). Genome sequence of the Brown Norway rat yields insights into mammalian evolution. Nature, 428(6982), 493-521. (Year: 2004).*
Vander Heiden et al. 2018. Direct Submission. Submitted Apr. 9, 2018. (Year: 2018).*
Chen et al. (2020). CN 111704666 A. Machine Translation. (Year: 2020).*
Lin. (2020). CN 111398583 A. Machine Translation. (Year: 2020).*
Guo, L. et al. (2020). Profiling Early Humoral Response to Diagnose Novel Coronavirus Disease (COVID-19). Clinical infectious diseases: an official publication of the Infectious Diseases Society of America, 71(15), 778-785. (Year: 2020).*
Burbelo P.D., et al. Sensitivity in Detection of Antibodies to Nucleocapsid and Spike Proteins of Severe Acute Respiratory Syndrome Coronavirus 2 in Patients With Coronavirus Disease 2019. J Infect Dis. Jun. 29, 2020;222(2):206-213. (Year: 2020).*
Bowie JU, Reidhaar-Olson JF, Lim WA, Sauer RT. Deciphering the message in protein sequences: tolerance to amino acid substitutions. Science. Mar. 16, 1990;247(4948):1306-10 (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14 (Year: 2000).*
Kussie, P., Parhami-Seren, B., Wysocki, L., & Margolies, M. (1994). A single engineered amino acid substitution changes antibody fine specificity. The Journal of Immunology (1950), 152(1), 146-152. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714 (Year: 2015).*
Sela-Culang I, Kunik V, Ofran Y. The structural basis of antibody-antigen recognition. Front Immunol. Oct. 8, 2013;4:302. (Year: 2013).*

(Continued)

*Primary Examiner* — Rachel B Gill
*Assistant Examiner* — Carey Alexander Stuart
(74) *Attorney, Agent, or Firm* — Sughrue Mion, PLLC

(57) ABSTRACT

A method for measuring a viral antigen using a capture antibody and a detection antibody. The method includes forming a sandwich immune complex that contains the capture antibody, the viral antigen and the detection antibody. The capture antibody includes specific sequences of CDRs and the detection antibody includes specific sequences of CDRs.

18 Claims, 3 Drawing Sheets

Specification includes a Sequence Listing.

(56) References Cited

OTHER PUBLICATIONS

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Collis, A. V., Brouwer, A. P., & Martin, A. C. (2003). Analysis of the antigen combining site: correlations between length and sequence composition of the hypervariable loops and the nature of the antigen. Journal of molecular biology, 325(2), 337-354. (Year: 2003).*

Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Patrick, D. M. et al. (2006). An Outbreak of Human Coronavirus OC43 Infection and Serological Cross-reactivity with SARS Coronavirus. The Canadian Journal of Infectious Diseases & Medical Microbiology, 17(6), 330-336. (Year: 2006).*

Sun, Z. F., & Meng, X. J. (2004). Antigenic cross-reactivity between the nucleocapsid protein of severe acute respiratory syndrome (SARS) coronavirus and polyclonal antisera of antigenic group I animal coronaviruses: implication for SARS diagnosis. Journal of Clinical Microbiology, 42(5), 2351-2352. (Year: 2004).*

Tamminen, K., Salminen, M., & Blazevic, V. (2021). Seroprevalence and SARS-CoV-2 cross-reactivity of endemic coronavirus OC43 and 229E antibodies in Finnish children and adults. Clinical Immunology, 229, 108782-108782. (Year: 2021).*

Lustig, Y. et al. (2021). Potential Antigenic Cross-reactivity Between Severe Acute Respiratory Syndrome Coronavirus 2 (SARS-CoV-2) and Dengue Viruses. Clinical Infectious Diseases, 73(7), e2444-e2449. (Year: 2021).*

De-Simone, S. G., Napoleão-Pêgo, P., Lechuga, G. C., Carvalho, J. P. R. S., Monteiro, M. E., Morel, C. M., & Provance, J. (2023). Mapping IgA Epitope and Cross-Reactivity between Severe Acute Respiratory Syndrome-Associated Coronavirus 2 and DENV. Vaccines, 11(12), 1749. (Year: 2023).*

Cox KL, Devanarayan V, Kriauciunas A, et al. Immunoassay Methods. May 1, 2012 [Updated Jul. 8, 2019]. In: Markossian S, Grossman A, Arkin M, et al., editors. Assay Guidance Manual [Internet]. Bethesda (MD): Eli Lilly & Company and the National Center for Advancing Translational Sciences; 2004 (Year: 2012).*

Jacksonimmuno.com Posted Aug. 3, 2023. [retrieved on Sep. 23, 2024]. Retrieved from the Internet: <URL: https://www.jacksonimmuno.com/secondary-antibody-resource/immuno-techniques/sandwich-elisa/> Posted Aug. 3, 2023, (Year: 2023).*

Bio-rad-antibodies.com. [retrieved on Sep. 23, 2024]. Retrieved from the Internet. <URL: https://www.bio-rad-antibodies.com/elisa-types-direct-indirect-sandwich-competition-elisa-formats.html#Sandwich> (Year: 2024).*

Extended European search report issued on Dec. 14, 2021 in a counterpart European patent application No. 21188360.8.

Li Zhang et al., "Development of Patient-Derived Human Monoclonal Antibodies Against Nucleocapsid Protein of Severe Acute Respiratory Syndrome Coronavirus 2 for Coronavirus Disease 2019 Diagnosis", Frontiers in Immunology, Nov. 13, 2020, pp. 1-11, vol. 11, Article 595970.

Kentaro Yamakawa et al., "Development of Reagent for Detection of Novel Coronavirus SARS-CoV-2 Antigen Using Immunochromatography", Japanese Journal of Medicine and Pharmaceutics Science, Jun. 2020, pp. 937-944, vol. 77, No. 6.

Qiaozhen Ye et al., "Architecture and self-assembly of the SARS-CoV-2 nucleocapsid protein", Protein Science, Jul. 2020, pp. 1890-1901, vol. 29.

Hiroaki Kariwa et al., "Characterization and epitope mapping of monoclonal antibodies to the nucleocapsid protein of severe acute respiratory syndrome coronavirus", Japanese Journal of Veterinary Research, 2008, pp. 115-127, vol. 55, No. 4.

Wei Feng et al., "Molecular Diagnosis of COVID-19: Challenges and Research Needs", Analytical Cemistry, Jun. 23, 2020, pp. 10196-10209, vol. 92.

Japanese Office Action issued on Aug. 24, 2021 in a counterpart Japanese patent application No. 2020-128480.

"SARS-CoV-2 (2019-nCoV) Nucleoprotein/NP Elisa Kit", Catalog No. KIT40588, Sino Biological, User's manual, 28 pages.

"SARS-CoV-2 Antigen Elisa Kit", Catalog No. DEIA2020, Creative Diagnostics, User's manual, 12 pages.

Kotaro Fujimoto et al., "Sensitive and Specific Enzyme-Linked Immunosorbent Assay Using Chemiluminescence for Detection of Severe Acute Respiratory Syndrome Viral Infection", Journal of Clinical Microbiology, Jan. 2008, pp. 302-310, vol. 46, No. 1.

Chinese Office Action issued on May 20, 2024 in a counterpart Chinese patent application No. 202110793411.0.

* cited by examiner

SEQUENCE LISTING

```
<160> NUMBER OF SEQ ID NOS: 19

<210> SEQ ID NO 1
<211> LENGTH: 7
<212> TYPE: PRT
<213> ORGANISM: Mus musculus

<400> SEQUENCE: 1

Thr Ser Gly Thr Gly Val Ser
1               5

<210> SEQ ID NO 2
<211> LENGTH: 16
<212> TYPE: PRT
<213> ORGANISM: Mus musculus

<400> SEQUENCE: 2

His Ile Tyr Trp Asp Asp Asp Lys Arg Tyr Asn Pro Ser Leu Lys Ser
1               5                   10                  15

<210> SEQ ID NO 3
<211> LENGTH: 9
<212> TYPE: PRT
<213> ORGANISM: Mus musculus

<400> SEQUENCE: 3

Ser Asn Tyr Gly Tyr Asp Leu Asp Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asn Val Gly Thr Asn Val Val
1               5                   10

<210> SEQ ID NO 5
<211> LENGTH: 7
<212> TYPE: PRT
<213> ORGANISM: Mus musculus

<400> SEQUENCE: 5

Ser Ala Ser Tyr Arg Tyr Ser
1               5

<210> SEQ ID NO 6
<211> LENGTH: 9
<212> TYPE: PRT
```

```
<213> ORGANISM: Mus musculus

<400> SEQUENCE: 6

Gln Gln Tyr Asn Asn Tyr Pro Leu Thr
1               5

<210> SEQ ID NO 7
<211> LENGTH: 5
<212> TYPE: PRT
<213> ORGANISM: Mus musculus

<400> SEQUENCE: 7

Asp Tyr Tyr Met Tyr
1               5

<210> SEQ ID NO 8
<211> LENGTH: 17
<212> TYPE: PRT
<213> ORGANISM: Mus musculus

<400> SEQUENCE: 8

Thr Ile Ser Asp Gly Gly Ser Tyr Thr Tyr Tyr Pro Asp Ser Val Lys
1               5                   10                  15

Gly

<210> SEQ ID NO 9
<211> LENGTH: 10
<212> TYPE: PRT
<213> ORGANISM: Mus musculus

<400> SEQUENCE: 9

Ala Ala Asp Tyr Gly Gly Tyr Phe Asp Tyr
1               5                   10

<210> SEQ ID NO 10
<211> LENGTH: 8
<212> TYPE: PRT
<213> ORGANISM: Mus musculus

<400> SEQUENCE: 10

Ser Ala Ser Gln Gly Ile Ser Asn
1               5

<210> SEQ ID NO 11
<211> LENGTH: 7
<212> TYPE: PRT
<213> ORGANISM: Mus musculus

<400> SEQUENCE: 11

Tyr Thr Ser Ser Leu His Ser
1               5

<210> SEQ ID NO 12
<211> LENGTH: 9
<212> TYPE: PRT
<213> ORGANISM: Mus musculus

<400> SEQUENCE: 12

Gln Gln Tyr Ser Lys Leu Pro Tyr Thr
1               5

<210> SEQ ID NO 13
<211> LENGTH: 119
<212> TYPE: PRT
```

```
<213> ORGANISM: Mus musculus

<400> SEQUENCE: 13

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Thr Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Val Ser Lys Asp Thr Ser Gly Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Asn Tyr Gly Tyr Asp Leu Asp Tyr Trp Gly Gln Gly
            100                 105                 110

Thr Thr Leu Thr Val Ser Ser
            115

<210> SEQ ID NO 14
<211> LENGTH: 109
<212> TYPE: PRT
<213> ORGANISM: Mus musculus

<400> SEQUENCE: 14

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ser Gly Thr Lys Leu Glu Ile Lys Arg Ala
            100                 105

<210> SEQ ID NO 15
<211> LENGTH: 119
<212> TYPE: PRT
<213> ORGANISM: Mus musculus

<400> SEQUENCE: 15

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80
```

Leu Gln Met Ser Ser Leu Lys Ser Asp Asp Thr Ala Lys Tyr Tyr Cys
                85                  90                  95

Ala Arg Ala Ala Asp Tyr Gly Gly Tyr Phe Asp Tyr Trp Gly Gln Gly
            100                 105                 110

Thr Thr Leu Thr Val Ser Ser
        115

<210> SEQ ID NO 16
<211> LENGTH: 109
<212> TYPE: PRT
<213> ORGANISM: Mus musculus

<400> SEQUENCE: 16

Asp Ile Gln Leu Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg Ala
            100                 105

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 17
cacattggca cccgcaatc                                                  19

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
gaggaacgag aagaggcttg                                                 20

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 19
acttcctcaa ggaacaacat tgcca                                           25

METHOD FOR MEASURING VIRAL ANTIGEN IN SAMPLE, ANTIBODY SET, AND REAGENT KIT

CROSS REFERENCE TO RELATED APPLICATIONS

This application claims priority from prior Japanese Patent Application No. 2020-128480, filed on Jul. 29, 2020, entitled "METHOD FOR MEASURING VIRAL ANTIGEN IN SAMPLE, ANTIBODY SET, AND REAGENT KIT", the entire contents of which are incorporated herein by reference.

The instant application contains a Sequence Listing which has been filed electronically in ASCII format and is hereby incorporated by reference in its entirety. Said ASCII copy, created on Jun. 28, 2021, is named SEQ_LISTING_REV_TXT and is 7 KB in size.

FIELD OF THE INVENTION

The present invention relates to a method for measuring a viral antigen in a sample by using a capture antibody and a detection antibody. The present invention relates to an antibody set for measuring a viral antigen in a sample by an immunological measurement method. The present invention relates to a reagent kit that contains a capture antibody and a detection antibody.

BACKGROUND

Measurement of a viral antigen in a sample has been known to determine whether a target virus is present in the sample or not. For example, an instruction manual of SARS-CoV-2 (2019-nCoV) Nucleoprotein/NP ELISA Kit (catalog number: KIT40588) from Sino Biological Inc., and an instruction manual of SARS-CoV-2 NP Antigen ELISA Kit (DEIA2020) from Creative Diagnostics describe reagent kits for measuring a nucleoprotein of SARS-CoV-2 in a sample according to enzyme-linked immunosorbent assay (ELISA method), by using a capture antibody and a detection antibody.

An object of the present invention is to provide a novel antibody set capable of measuring a nucleoprotein of SARS-CoV-2 in a sample, a measurement method with use of the antibody set, and a reagent kit.

SUMMARY OF THE INVENTION

The scope of the present invention is defined solely by the appended claims, and is not affected to any degree by the statements within this summary.

The present invention provides a method for measuring a viral antigen in a sample by using a capture antibody and a detection antibody, the method comprising: forming a sandwich immune complex that contains the capture antibody, the viral antigen and the detection antibody, the capture antibody comprising a heavy chain variable region that comprises CDR1 comprising amino acid sequence of SEQ ID NO: 1, CDR2 comprising amino acid sequence of SEQ ID NO: 2 and CDR3 comprising amino acid sequence of SEQ ID NO: 3, and a light chain variable region that comprises CDR1 comprising amino acid sequence of SEQ ID NO: 4, CDR2 comprising amino acid sequence of SEQ ID NO: 5 and CDR3 comprising amino acid sequence of SEQ ID NO: 6, and the detection antibody comprising a heavy chain variable region that comprises CDR1 comprising amino acid sequence of SEQ ID NO: 7, CDR2 comprising amino acid sequence of SEQ ID NO: 8 and CDR3 comprising amino acid sequence of SEQ ID NO: 9, and a light chain variable region that comprises CDR1 comprising amino acid sequence of SEQ ID NO: 10, CDR2 comprising amino acid sequence of SEQ ID NO: 11 and CDR3 comprising amino acid sequence of SEQ ID NO: 12.

The present invention also provides an antibody set for measuring a viral antigen in a sample by an immunological measurement method, the antibody comprising a capture antibody and a detection antibody that form a sandwich immune complex with the viral antigen in the immunological measurement method, the capture antibody comprising a heavy chain variable region that comprises CDR1 comprising amino acid sequence of SEQ ID NO: 1, CDR2 comprising amino acid sequence of SEQ ID NO: 2 and CDR3 comprising amino acid sequence of SEQ ID NO: 3; and a light chain variable region that comprises CDR1 comprising the amino acid sequence of SEQ ID NO: 4, CDR2 comprising the amino acid sequence of SEQ ID NO: 5 and CDR3 comprising the amino acid sequence of SEQ ID NO: 6, and the detection antibody comprises a heavy chain variable region that comprises CDR1 comprising amino acid sequence of SEQ ID NO: 7, CDR2 comprising amino acid sequence of SEQ ID NO: 8 and CDR3 comprising amino acid sequence of SEQ ID NO: 9; and a light chain variable region that comprises CDR1 comprising amino acid sequence of SEQ ID NO: 10, CDR2 comprising amino acid sequence of SEQ ID NO: 11 and CDR3 comprising amino acid sequence of SEQ ID NO: 12.

The present invention provides a reagent kit that contains the capture antibody and the detection antibody.

According to the present invention, a novel antibody set capable of measuring a nucleoprotein of SARS-CoV-2 in a sample, a measurement method with use of the antibody set, and a reagent kit are provided.

DETAILED DESCRIPTION OF THE PREFERRED EMBODIMENTS

Figure 1A:
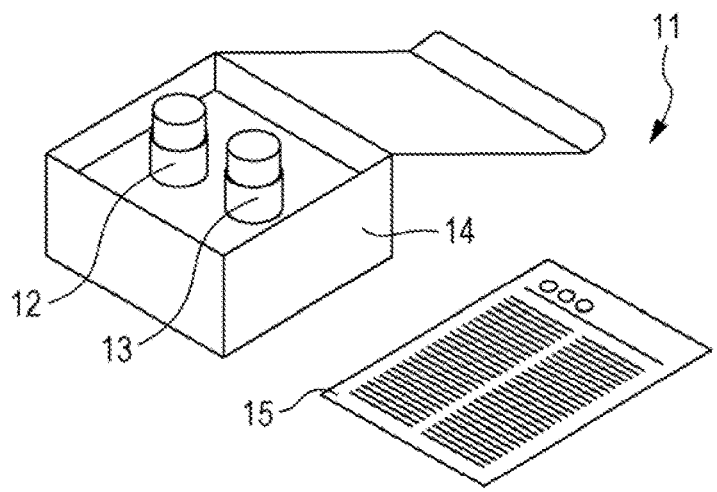
FIG. 1A is a schematic drawing illustrating an exemplary reagent kit of this embodiment.

The method for measuring a viral antigen of this embodiment (also referred to as "measurement method", hereinafter) measures in vitro a viral antigen in a sample, by an immunological measurement method with use of a capture antibody and a detection antibody each containing predetermined CDRs. In this embodiment, the capture antibody means an antibody that specifically binds to a test substance. When immobilized on a solid phase, the capture antibody can capture the test substance on the solid phase. The detection antibody means an antibody that specifically binds to a test substance. When labeled with a labeling substance, the detection antibody can provide a detectable signal. Although the detection antibody is not immobilized on a solid phase in most cases, the labeling substance per se may occasionally serve as a solid phase typically in the form of particle.

The immunological measurement method is not specially limited as long as it includes forming a sandwich immune complex. The sandwich immune complex means a complex that contains the capture antibody, the test substance and the detection antibody, in which the capture antibody and the detection antibody are bound to different sites of the test substance. This sort of immunological measurement method is exemplified by sandwich ELISA method and immunochromatography method. Among them, the sandwich ELISA method is particularly preferred. The sandwich ELISA method applicable here may be an immune complex transfer method described in Japanese Patent Application Laid-Open No. H01-254868.

In this patent specification, the term "measuring a viral antigen" encompasses acquiring a measured value of a viral antigen, and, quantifying the amount or concentration of a viral antigen in a sample. The measured value of the viral antigen may be a value that reflects the amount or concentration of the viral antigen in the sample. The "value that reflects the amount or concentration" is a value that depends on the type of the labeling substance described later, and is exemplified by measured value of luminescence intensity, measured value of fluorescence intensity, measured value of radiation intensity, and measured value of optical density. The value of the amount or concentration of the viral antigen in the sample can be determined, for example, on the basis of the measured value of the viral antigen and a measured value of a calibrator. The calibrator is a kind of control sample used for quantifying the test substance, which is a sample that contains a known concentration of the test substance or a corresponding standard substance.

The term "antibody" herein encompasses full-length antibody and fragment thereof. Class of antibody may be any of IgG, IgA, IgM, IgD and IgE, among which IgG is preferred. Subclass of IgG is not specially limited, and may be any of IgG1, IgG2, IgG3 and IgG4. The fragment of the antibody is exemplified by reduced IgG (rIgG), Fab, Fab', F(ab')$_2$, Fv, single chain antibody (scFv), diabody and triabody. Methods per se for preparing these antibody fragments have been already known. The antibody may be either monoclonal antibody or polyclonal antibody, where monoclonal antibody is preferred. The antibody may be derived from any animal including mouse, rat, hamster, rabbit, goat, horse, camel, alpaca and chicken. The antibody is preferably a murine monoclonal antibody.

In this embodiment, the capture antibody and the detection antibody may be, equally or differently, full-length antibody or antibody fragment. When both of the capture antibody and the detection antibody are antibody fragments, type of the fragments may be same or different between the capture antibody and the detection antibody. Both of the capture antibody and the detection antibody may preferably be monoclonal antibodies.

In this embodiment, the capture antibody includes a heavy chain variable region that includes CDR1 having amino acid sequence of SEQ ID NO: 1, CDR2 having amino acid sequence of SEQ ID NO: 2, and CDR3 having amino acid sequence of SEQ ID NO: 3. The capture antibody includes a light chain variable region that includes CDR1 having amino acid sequence of SEQ ID NO: 4, CDR2 having amino acid sequence of SEQ ID NO: 5 and CDR3 having amino acid sequence of SEQ ID NO: 6. The amino acid sequences of the individual CDRs of the capture antibody are enumerated below. Hereinafter, CDRH1, CDRH2 and CDRH3 represent CDR1, CDR2 and CDR3 of the heavy chain, respectively. CDRL1, CDRL2 and CDRL3 represent CDR1, CDR2 and CDR3 of the light chain, respectively. Amino acid sequences of the individual CDRs are those determined on the basis of the Kabat method. In this patent specification, "based on the Kabat method" means that the numbering of the amino acid residues in the CDR and the variable region follows the numbering scheme advocated by Kabat et al. (see Kabat E. A. et al., Sequences of Proteins of Immunological Interest, 5th ed. Public Health Service, National Institutes of Health, Bethesda, MD (1991), NIH Publication No. 91-3242).

[Amino Acid Sequences of CDRs of Capture Antibody]

```
CDRH1:
                                        (SEQ ID NO: 1)
TSGTGVS

CDRH2:
                                        (SEQ ID NO: 2)
HIYWDDDKRYNPSLKS

CDRH3:
                                        (SEQ ID NO: 3)
SNYGYDLDY

CDRL1:
                                        (SEQ ID NO: 4)
KASQNVGTNVV

CDRL2:
                                        (SEQ ID NO: 5)
SASYRYS

CDRL3:
                                        (SEQ ID NO: 6)
QQYNNYPLT
```

In this embodiment, the detection antibody includes a heavy chain variable region that includes CDR1 having amino acid sequence of SEQ ID NO: 7, CDR2 having amino acid sequence of SEQ ID NO: 8, and CDR3 having amino acid sequence of SEQ ID NO: 9. The detection antibody includes a light chain variable region that includes CDR1 having amino acid sequence of SEQ ID NO: 10, CDR2 having amino acid sequence of SEQ ID NO: 11 and CDR3 having amino acid sequence of SEQ ID NO: 12. Amino acid sequences of the individual CDRs of the detection antibody are enumerated below. Amino acid sequences of the individual CDRs are those determined on the basis of the Kabat method.

[Amino Acid Sequences of CDRs of Detection Antibody]

```
CDRH1:
                                        (SEQ ID NO: 7)
DYYMY

CDRH2:
                                        (SEQ ID NO: 8)
TISDGGSYTYYPDSVKG

CDRH3:
                                        (SEQ ID NO: 9)
AADYGGYFDY
```

-continued

CDRL1:
(SEQ ID NO: 10)
SASQGISN

CDRL2:
(SEQ ID NO: 11)
YTSSLHS

CDRL3:
(SEQ ID NO: 12)
QQYSKLPYT

Although the capture antibody that includes six CDRs respectively having amino acid sequences of SEQ ID NOs: 1 to 6, and the detection antibody that includes six CDRs respectively having amino acid sequences of SEQ ID NOs: 7 to 12 can specifically bind to the same viral antigen, epitopes recognized by them are different from each other. Therefore, the capture antibody and the detection antibody bind to the viral antigen, thereby forming a sandwich immune complex.

In one embodiment, the capture antibody may be a humanized antibody that includes six CDRs respectively having amino acid sequences of SEQ ID NOs: 1 to 6. The detection antibody may be a humanized antibody that includes six CDRs respectively having amino acid sequences of SEQ ID NOs: 7 to 12. The humanized antibody is an antibody obtained by transplanting a gene sequence of CDR of a non-human-derived antibody into a human antibody gene, by a known CDR grafting method.

The capture antibody may include a heavy chain variable region having amino acid sequence of SEQ ID NO: 13, as the heavy chain variable region that includes CDRH1, CDRH2 and CDRH3, respectively having amino acid sequences of SEQ ID NOs: 1 to 3. The capture antibody may include a light chain variable region having amino acid sequence of SEQ ID NO: 14, as the light chain variable region that includes CDRL1, CDRL2 and CDRL3, respectively having amino acid sequences of SEQ ID NOs: 4 to 6. The amino acid sequences of the variable regions, represented by SEQ ID NOs: 13 and 14, are shown below. Underlined parts indicate CDRs. The amino acid sequences of these variable regions are those determined on the basis of the Kabat method.

[Amino Acid Sequences of Variable Regions of Capture Antibody]

-Heavy Chain Variable Region
(SEQ ID NO: 13)
QVTLKESGPGILQPSQTLSLTCSFSGFSLSTSGTGVSWIRQPSGKGLEWL
AHIYWDDDKRYNPSLKSRLTVSKDTSGNQVFLKITSVDTADTATYYCARS
NYGYDLDYWGQGTTLTVSS -Light Chain Variable Region
(SEQ ID NO: 14)
DIVMTQSQKFMSTSVGDRVSVTCKASQNVGTNVVWYQQKPGQSPKA
LIYSASYRYSGVPDRFTGSGSGTDFTLTISNVQSEDLAEYFCQQYNNYPL
TFGSGTKLEIKRA The detection antibody may include a heavy chain variable region having amino acid sequence of SEQ ID NO: 15, as the heavy chain variable region that includes CDRH1, CDRH2 and CDRH3, respectively having amino acid sequences of SEQ ID NOs: 7 to 9. The detection antibody may include a light chain variable region having amino acid sequence of SEQ ID NO: 16, as the light chain variable region that includes CDRL1, CDRL2 and CDRL3, respectively having amino acid sequences of SEQ ID NOs: 10 to 12. The amino acid sequences of the variable regions, represented by SEQ ID NOs: 15 and 16, are shown below. Underlined parts indicate CDRs. The amino acid sequences of these variable regions are those determined on the basis of the Kabat method.

[Amino Acid Sequences of Variable Regions of Detection Antibody]

-Heavy Chain Variable Region
(SEQ ID NO: 15)
EVQLVESGGGLVKPGGSLKLSCAASGFTFSDYYMYWVRQTPEKRLEW
VATISDGGSYTYYPDSVKGRFTISRDNAKNNLYLQMSSLKSDDTAKYYC
ARAADYGGYFDYWGQGTTLTVSS -Light Chain Variable Region
(SEQ ID NO: 16)
DIQLTQTTSSLSASLGDRVTISCSASQGISNYLNWYQQKPDGTVKLLIY
YTSSLHSGVPSRFSGSGSGTDYSLTISNLEPEDIATYYCQQYSKLPYTF
GGGTKLEIKRA In one embodiment, the capture antibody may also be a chimeric antibody that includes the heavy chain variable region having amino acid sequence of SEQ ID NO: 13, and the light chain variable region having amino acid sequence of SEQ ID NO: 14. The detection antibody may also be a chimeric antibody that includes the heavy chain variable region having amino acid sequence of SEQ ID NO: 15, and the light chain variable region having amino acid sequence of SEQ ID NO: 16. The chimeric antibody is an antibody in which a variable region of an antibody derived from a certain species and a constant region of an antibody derived from a different species are joined.

The capture antibody and the detection antibody in this embodiment may have the amino acid sequences modified so as not to reduce the binding activity towards viral antigen. Such modification of the amino acid sequence is exemplified by substitution, deletion, addition and/or insertion of amino acid residue. The site where the amino acid sequence of each antibody is modified may reside either in the constant region or in the variable region, and either in the heavy chain or in the light chain. The variable region, when modified, is preferably modified in the framework region (FR). FR means a region other than CDR, which resides in each of the light chain variable region and the heavy chain variable region of the antibody. FRs serve as a scaffold that links the three CDRs, and contributes to structural stability of CDRs. The amino acid sequence of an antibody may be modified by introducing a mutation into an antibody gene, with use of a known technique such as DNA recombination or other molecular biological techniques.

The number of amino acid residues to be modified is usually 10 residues or less, preferably 5 residues or less, and more preferably 3 residues or less. Type of modification of the amino acid sequence of the antibody is preferably conservative substitution. Conservative substitution means substitution of an amino acid residue with some other amino acid residue having a side chain chemically similar to the side chain of the original residue. Conservative substitution per se of amino acid sequences is known in the art. Alternatively, the amino acid sequence of the antibody may be modified by a method for controlling affinity of the antibody for an antigen, which includes modification of amino acid residue in FR3 of the antibody, as described in U.S. Patent Application Publication No. 2018/0179298. The amino acid sequence of an antibody may be modified alternatively by a method for improving thermal stability of an antibody, which includes substituting the 80th amino acid residue in the variable region and the 171st amino acid residue in the constant region of the antibody, with cysteine as described in U.S. Patent Application Publication No. 2019/0040119.

The capture antibody in this embodiment may be preliminarily immobilized on a solid phase. Mode of immobilization of the capture antibody on the solid phase is not specially limited. For example, the capture antibody and the solid phase may be directly bound, or the capture antibody and the solid phase may be indirectly bound through some other substance. The direct binding is exemplified by physical adsorption. The indirect binding is exemplified by immobilizing a molecule specifically bindable with an antibody on the solid phase, and then binding the antibody to the molecule, thereby immobilizing the antibody on the solid phase. The molecule specifically bindable with an antibody is exemplified by protein A or G, and an antibody that specifically recognizes the antibody (secondary antibody). The capture antibody may also be immobilized on the solid phase, with use of combination of substances interposed between the antibody and the solid phase. Such combination of substances is exemplified by combination of biotins and avidins, and combination of hapten and anti-hapten antibody. The biotins include biotin, and biotin analogs such as desthiobiotin and oxybiotin. The avidins include avidin, and avidin analogs such as streptavidin and Tamavidin (registered trademark). The combination of hapten and anti-hapten antibody is exemplified by combination of a compound having 2,4-dinitrophenyl (DNP) group and anti-DNP antibody. For example, by using a capture antibody preliminarily modified with any of biotins (or a compound having DNP group), and a solid phase having any of avidins (or anti-DNP antibody) preliminarily immobilized thereon, the capture antibody may be immobilized on the solid phase, making use of binding between biotin and avidin (or binding between DNP group and anti-DNP antibody).

Material for composing the solid phase is not specially limited, and is typically selectable from organic polymer compound, inorganic compound and biopolymer. The organic polymer compound is exemplified by latex, polystyrene and polypropylene. The inorganic compound is exemplified by magnetic substance (iron oxide, chromium oxide, ferrite, etc.), silica, alumina and glass. The biopolymer is exemplified by insoluble agarose, insoluble dextran, gelatin and cellulose. Two or more of them may be used in combination. Shape of the solid phase is not specially limited, and is exemplified by particle, membrane, microplate, microtube and test tube. Among them, particle and microplate are preferred. The particles is particularly preferably magnetic particle.

In this embodiment, the detection antibody may also be preliminarily labeled with a labeling substance. The labeling substance is not specially limited, and is exemplified by a substance that can generate a signal by itself (also referred to as "signal generating substance", hereinafter), and a substance that catalyzes reaction of some other substance to generate a signal. The signal generating substance is exemplified by fluorescent substance, radioisotope, and color developing substance. The substance that catalyzes reaction of some other substance to generate a detectable signal is exemplified by enzyme. The fluorescent substance is exemplified by fluorescent dyes such as fluorescein isothiocyanate (FITC), rhodamine and Alexa Fluor (registered trademark); and fluorescent proteins such as GFP. Examples of the radioisotope include $^{125}I$, $^{14}C$ and $^{32}P$. The color developing substance is exemplified by metal colloids such as gold nanocolloid. The enzyme is exemplified by alkaline phosphatase, peroxidase, β-galactosidase, glucosidase, polyphenol oxidase, tyrosinase, acid phosphatase and luciferase. Enzyme is preferred as the labeling substance, for which alkaline phosphatase is particularly preferred.

In this embodiment, a labeled secondary antibody may be used as the labeling substance. The labeled secondary antibody means an antibody that is labeled with the labeling substance, and can specifically recognize the detection antibody. As a result of binding of the labeled secondary antibody to the detection antibody, the detection antibody is indirectly labeled with the labeling substance.

The capture antibody and the detection antibody may be prepared by a known technique such as DNA recombination technique or other molecular biological technique, typically as described below. First, RNA is extracted from a hybridoma that produces any murine antibody. The hybridoma is obtainable by a known method such as described in Kohler G. and Milstein C., *Nature*, vol. 256, pp. 495-497, 1975. By using the extracted RNA, polynucleotides that individually encode the heavy chain and the light chain of the antibody are synthesized according to a reverse transcription reaction and rapid amplification of cDNA ends (RACE). In these polynucleotides, the individual base sequences that encode CDRH1, CDRH2, CDRH3, CDRL1, CDRL2 and CDRL3 are substituted respectively with base sequences that encode amino acid sequences of SEQ ID NOs: 1 to 6, or SEQ ID NOs: 7 to 12 by the PCR method, whereby polynucleotides that individually code the heavy chain and the light chain of the capture antibody or the detection antibody are obtainable. Alternatively, in polynucleotides that encode the heavy chain of any murine antibody, the base sequence that encodes the variable region may be substituted with the base sequence that encodes amino acid sequence SEQ ID NO: 13 or 15, and the base sequence of a region that encodes the variable region in the polynucleotide that encodes the light chain of the antibody may be substituted with the base sequence that encodes amino acid sequence of SEQ ID NO: 14 or 16. The obtained polynucleotide is integrated into a known expression vector. The polynucleotide that encodes the heavy chain and the polynucleotide that encodes the light chain may be integrated into a single expression vector so that each of them can be expressed independently, or may be separately integrated into two expression vectors. In this way, the expression vector that contains the polynucleotides that encode the heavy chain and the light chain of the capture antibody or the detection antibody is acquired. Type of the expression vector is not specially limited, and may be expression vector for mammalian cell or expression vector for *E. coli*. The capture antibody or the detection antibody is obtainable by integrating the thus obtained expression vector into a suitable host cell (mammalian cell or *E. coli*, for example), by transformation or transfection. The capture antibody and the detection antibody as humanized antibodies may also be produced by using the base sequences that encodes amino acid sequences of SEQ ID NOs: 1 to 6 and SEQ ID NOs: 7 to 12, according to the known CDR grafting method (see, Jones P. T. et al., *Nature*, vol. 321, pp. 522-525, 1986; Co M. S. et al., *Proc. Natl. Acad. Sci. USA*, vol. 93, pp. 7843-7848, 1996, for example).

In this embodiment, the viral antigen is not specially limited as long as it binds to the capture antibody and the detection antibody to form the sandwich immune complex. Such viral antigens is exemplified by nucleoproteins of SARS-CoV and nucleoprotein of SARS-CoV-2. Nucleoprotein (also referred to as "N protein", hereinafter) means a protein that coexists with viral nucleic acid, and is also called nucleocapsid protein.

If the capture antibody and/or the detection antibody do not specifically bind to the viral antigen, and therefore do not substantially form the sandwich immune complex, the viral antigen is not a target substance of the measurement method of this embodiment. In one embodiment, the capture antibody and the detection antibody form the sandwich immune complex with the N protein of SARS-CoV or SARS-CoV-2, but do not substantially form the sandwich immune complex with the N protein of MERS-CoV and viral antigens of HCoV-NL63, HCoV-229E and HCoV-OC43 (viral lysates that contain N protein, for example).

In this embodiment, the sample encompasses not only a sample that contains viral antigen or viral antigen-containing virus, but also a sample suspected of containing viral antigen or viral antigen-containing virus. As this sort of sample, a biological sample is suitably used. The biological sample means a sample collected from living body. The biological sample is exemplified by nasopharyngeal swab specimen, saliva, nasal secretion, sputum, whole blood, plasma, serum, bronchoalveolar lavage fluid, cerebrospinal fluid and lymph fluid. Besides the biological sample, employable are excreta, sewage, river water, sea water and soil. The excreta include urine and feces.

The sample in this embodiment is preferably in liquid form. The liquid sample is not limited to solution, and encompass suspension and sol. The sample, if not in liquid form, may be converted to liquid by adding thereto an appropriate aqueous medium. Such aqueous medium is not specially limited as long as it does not interfere with measurements described later, and is exemplified by water, saline and buffer solution. The buffer solution is not specially limited as long as it can demonstrate buffering action at pH around neutral (pH of 6 or higher and 8 or lower, for example). Such buffer is exemplified by Good's buffers such as ACES, HEPES, MES and PIPES; triethanolamine hydrochloride buffer, Tris hydrochloride buffer, phosphate buffered saline (PBS) and Tris buffered saline (TBS). Any insoluble impurity, if found to reside in the liquid sample, may be removed from the sample by a known technique such as centrifugation or filtration. The liquid sample may optionally be diluted with the aqueous medium described above.

For the sample that contains the viral antigen-containing virus, an extraction reagent may be added to the sample in order to release the viral antigen from the virus. The extraction reagent means a reagent that lyses virus in a sample, and enables extraction of the viral antigen such as N protein. Such reagent is exemplified by buffer solution that contains a surfactant. The surfactant is not specially limited as long as it does not interfere with the measurement described later, and is exemplified by NP-40, Tween (registered trademark)-20 and Triton (registered trademark) X-100. A commercially available extraction reagent may be employable. The extraction reagent may include a chelating agent. The chelating agent is exemplified by sodium salt or potassium salt of ethylenediaminetetraacetic acid (EDTA).

In the measurement method of this embodiment, first, the sandwich immune complex that contains the capture antibody, the viral antigen and the detection antibody is formed. The sandwich immune complex may be formed by mixing a sample that expectedly contains a viral antigen, the capture antibody, and the detection antibody. In a preferred embodiment, the sandwich immune complex that includes the capture antibody, the viral antigen and the detection antibody is formed on the solid phase. For example, the sample that expectedly contains a viral antigen, the capture antibody and the detection antibody are mixed to form the sandwich immune complex, and then a solution that contains the complex is contacted with the solid phase capable of immobilizing thereon the capture antibody, whereby the complex may be formed on the solid phase. Alternatively, the capture antibody preliminarily immobilized on the solid phase may be employed. That is, the complex may be formed on the solid phase, by mixing the capture antibody immobilized on the solid phase, the sample that expectedly contains the target substance, and the detection antibody.

The measurement method of this embodiment includes detecting the sandwich immune complex formed on the solid phase. The viral antigen can be measured by detecting the sandwich immune complex on the solid phase by a method known in the art. For example, with use of the detection antibody labeled with a labeling substance, the viral antigen can be measured by detecting a signal generated by the labeling substance. With use of the labeled secondary antibody corresponded to the detection antibody, the viral antigen can be measured by detecting a signal generated by the labeling substance of the labeled secondary antibody bound to the detection antibody. In this embodiment, the detection antibody preliminarily labeled with a labeling substance is preferably used.

In this patent specification, "detecting a signal" encompasses qualitative detection of presence or absence of a signal, quantification of signal intensity, and semi-quantitative detection of the signal intensity. The semi-quantitative detection relies upon grade indication of the signal intensity which includes "no signal", "weak", "medium" and "strong", for example. In this embodiment, the signal intensity is preferably detected in a quantitative or semi-quantitative manner.

The method for detecting signal per se has been already known in the art. In this embodiment, it suffices that a measurement method adapted to the type of signal obtainable from the labeling substance is properly selected. For example, the signal of the labeling substance, if being an enzyme, is detectable by reacting the enzyme with a corresponded substrate, and by measuring the generated signal such as light or color with use of a known instrument such as a spectrophotometer.

The substrate for the enzyme is properly selectable from known substrates, depending on the type of enzyme. In an exemplary case where alkaline phosphatase is used as the enzyme, the substrate is exemplified by chemiluminescent substrates such as CDP-Star (registered trademark) (disodium 4-chloro-3-(methoxyspiro[1,2-dioxetane-3,2'-(5'-chloro)tricyclo[3.3.1.13,7]decane]-4-yl)phenylphosphate), and CSPD (registered trademark) (disodium 3-(4-methoxyspiro[1,2-dioxetane-3,2-(5'-chloro)tricyclo[3.3.1.13,7]decane]-4-yl)phenylphosphate); and chromogenic substrate such as 5-bromo-4-chloro-3-indolylphosphate (BCIP), disodium 5-bromo-6-chloro-indolyl phosphate, and p-nitrophenyl phosphate. In an exemplary case where peroxidase is used as the enzyme, the substrate is exemplified by chemiluminescent substrates such as luminol and derivatives thereof; and chromogenic substrates such as ammonium 2,2'-azino-bis(3-ethylbenzothiazoline-6-sulfonate) (ABTS), 1,2-phenylenediamine (OPD), and 3,3',5,5'-tetramethylbenzidine (TMB).

In a case where the labeling substance is a radioisotope, radiation as a signal may be measured by using a known instrument such as a scintillation counter. In a case where the labeling substance is a fluorescent substance, fluorescence as a signal may be measured by using a known instrument such as a fluorescence microplate reader. Excitation wavelength and fluorescence wavelength may properly be determined depending on the type of fluorescent substance employed.

Results of detection of the signal may be utilized as results of measurement of the viral antigen in the sample. In an exemplary case where a signal intensity is quantified, the measured value of the signal intensity per se, or a value acquired from the measured value may be used as the measured value of the viral antigen. The value acquired from the measured value of the signal intensity is exemplified by a value obtained by subtracting a measured value of a negative control or a background value, from the measured value. The negative control is properly selectable, and is exemplified by a buffer solution free of viral antigen.

In this embodiment, the amount or concentration value of the viral antigen in the sample may also be determined by reading, on an analytical curve, a value corresponded to the measured value of signal intensity. The analytical curve may be created on the basis of measured values of a plurality of calibrators. The measured values of the calibrators are obtainable by measuring the calibrators according to the measurement method of this embodiment, in the same way as for the sample. The analytical curve may be prepared by plotting the measured values of the plurality of calibrators on X-Y plane, having concentration of the viral antigen scaled on X-axis, and the measured value (signal intensity, for example) scaled on Y-axis, and by fitting thereto a straight line or a curve according to a known technique such as the least square method. In this embodiment, the calibrators may be prepared, typically by adding a recombinant viral antigen to a buffer solution free of viral antigen, while adjusting the concentration to freely selectable values. The calibrator free of viral antigen employable here may also be a buffer solution per se free of viral antigen.

The measurement method of this embodiment may be conducted on a commercially available automated immunoassay analyzer. The automated immunoassay analyzer is an instrument that automatically conducts preparation and immunoassay of a sample to be measured, and outputs a measurement result of a target substance, upon setting of the sample and entry of a command to start the measurement by the user. This sort of automated immunoassay analyzer is exemplified by HISCL Series (Sysmex Corporation) that includes HISCL (registered trademark)-5000 and HISCL-800, and HI-1000 (Sysmex Corporation). The HISCL Series instrument conducts the measurement according to the sandwich ELISA method, by using a magnetic particle as the solid phase.

In this embodiment, B/F (bound/free) separation for removing any unreacted free component not forming the complex may be interposed between formation of the sandwich immune complex and detection of the complex. The unreacted free component means a component that does not compose the sandwich immune complex. This is exemplified by excessive capture antibody and detection antibody that remain unbound to the viral antigen. Technique for the B/F separation is not specially limited, and may be conducted, if the solid phase is a particle, by centrifugation whereby only the solid phase having the complex captured thereon may be recovered. With the solid phase given as a container such as a microplate or a microtube, the B/F separation is enabled by removing a liquid that contains the unreacted free component. With the solid phase given as a magnetic particle, the B/F separation is enabled by removing a liquid that contains the unreacted free component under suction through a nozzle, while keeping the magnetic particle magnetically restrained by a magnet, which is preferred from the viewpoint of automation. After removing the unreacted free components, the solid phase having the complex captured thereon may be washed with a suitable aqueous medium such as PBS.

A further embodiment relates to an antibody set used for measuring a viral antigen in a sample by an immunological measurement method (also referred to as "antibody set", hereinafter). In this patent specification, the term "antibody set" means a combination of a plurality of antibodies that includes at least the capture antibody and the detection antibody used for the immunological measurement method. Details of the immunological measurement method are the same as those described for the measurement method of this embodiment. The antibody set of this embodiment includes the capture antibody and the detection antibody that form the sandwich immune complex with the viral antigen in the immunological measurement method. Details of the capture antibody and the detection antibody contained in the antibody set of this embodiment are same as those described for the measurement method of this embodiment. The antibody set of this embodiment is suitably used in the measurement method of this embodiment.

A further embodiment relates to a reagent kit that includes the capture antibody and the detection antibody (also referred to as a "reagent kit", hereinafter). The reagent kit of this embodiment is used for measuring the viral antigen in the sample by the immunological measurement method. The reagent kit of this embodiment contains one or more reagents. Details of the immunological measurement method, the capture antibody and the detection antibody are same as those described for the measurement method of this embodiment.

In one embodiment, the reagent kit includes a reagent that contains the capture antibody, and a reagent that contains the detection antibody. Form of the reagent that contains the antibody is not specially limited, and may be solid (powder, crystal or freeze-dried product, for example), or liquid (solution, suspension or emulsions, for example). For the reagent that contains the antibody in liquid form, the solvent is not specially limited as long as it can solubilize and store the antibody. The solvent is exemplified by water, saline, PBS, TBS and Good's buffers. The Good's buffers are exemplified by MES, Bis-Tris, ADA, PIPES, Bis-Tris-propane, ACES, MOPS, MOPSO, BES, TES, HEPES, HEPPS, Tricine, Tris, Bicine and TAPS.

The reagent that contains an antibody may contain any of known additives. The additives are exemplified by protein stabilizers such as bovine serum albumin (BSA), preservatives such as sodium azide, and inorganic salts such as sodium chloride.

In one embodiment, the reagent kit may include the reagent that contains the capture antibody, the reagent that contains the detection antibody, and a solid phase. Alternatively, the capture antibody may be preliminarily immobilized on the solid phase. Details of the solid phase are same as those described previously in relation to the measurement method of this embodiment. A preferred solid phase is magnetic particle or microplate.

The detection antibody may preliminarily be labeled with a labeling substance. The reagent kit may alternatively include the reagent that contains the capture antibody, the reagent that contains the detection antibody, and a reagent that contains a labeled secondary antibody. Details of the labeling substance and the labeled secondary antibody are same as those described previously in relation to the measurement method of this embodiment. A preferred labeling substance is an enzyme. The enzyme is exemplified by alkaline phosphatase, peroxidase, β-galactosidase, glucosidase, polyphenol oxidase, tyrosinase, acid phosphatase and luciferase. A preferred enzyme is alkaline phosphatase. For the detection antibody labeled with an enzyme, or for the reagent kit having enzyme-labeled secondary antibody contained therein, the reagent kit may further contain a substrate for the enzyme. Details of the substrate are same as those described previously in relation to the measurement method of this embodiment.

The reagent kit of this embodiment may be provided with the individual reagents filled in vials and packaged in a box. Also a package insert may be enclosed in the box. The package insert may contain descriptions on contents of the reagent kit, compositions of the individual reagents, instructions for use and storage, and so forth.

An example of the reagent kit of this embodiment is illustrated in FIG. 1A. In FIG. 1A, reference numeral 11 denotes a reagent kit, reference numeral 12 denotes a first vial that contains a capture antibody-containing reagent, reference numeral 13 denotes a second vial that contains a detection antibody-containing reagent, reference numeral 14 denotes a packaging box, and reference numeral 15 denotes a package insert. In this example, the capture antibody may be immobilized on a solid phase (magnetic particles, for example). The detection antibody may be labeled with a labeling substance.

Figure 1B:
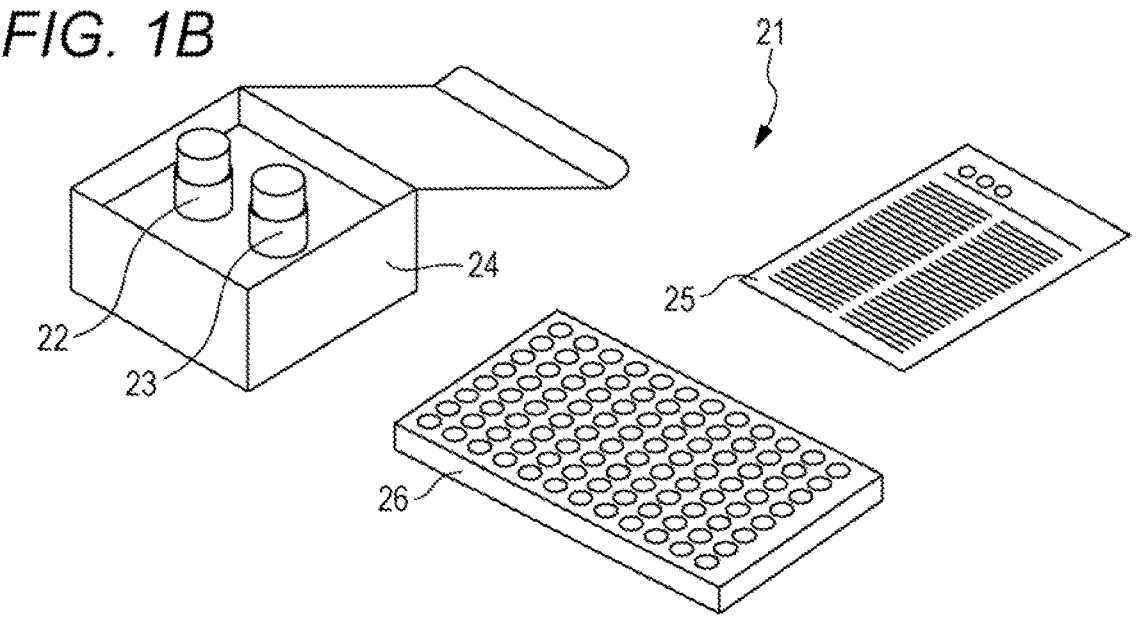
FIG. 1B is a schematic drawing illustrating an exemplary reagent kit of this embodiment.

An example of a reagent kit of another embodiment is illustrated in FIG. 1B. In FIG. 1B, reference numeral 21 denotes a reagent kit, reference numeral 22 denotes a first vial that contains a capture antibody-containing reagent, reference numeral 23 denotes a second vial that contains a detection antibody-containing reagent, reference numeral 24 denotes a packaging box, reference numeral 25 denotes a package insert, and reference numeral 26 denotes a microplate as the solid phase. In this example, the detection antibody may be labeled with a labeling substance.

Figure 1C:
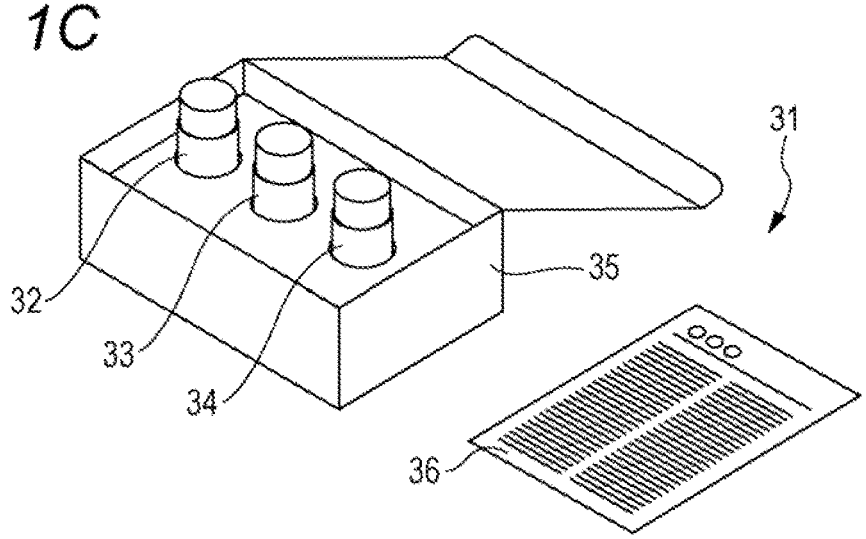
FIG. 1C is a schematic drawing illustrating an exemplary reagent kit of this embodiment.

An example of a reagent kit of still another embodiment is shown in FIG. 1C. In FIG. 1C, reference numeral 31 denotes a reagent kit, reference numeral 32 denotes a first vial that contains a capture antibody-containing reagent, reference numeral 33 denotes a second vial that contains a reagent containing an enzyme-labeled detection antibody, reference numeral 34 denotes a third vial that contains a reagent containing a substrate for the enzyme, reference numeral 35 denotes a packaging box, and reference numeral 36 denotes a package insert. In this example, the capture antibody may be immobilized on a solid phase (magnetic particles, for example).

The reagent kit of this embodiment may further contain a calibrator. The calibrator may include, for example, a buffer free of viral antigen (negative control), and a buffer that contains a known concentration of a recombinant viral antigen.

Hereinafter, the present disclosure will be described in further detail referring to Examples, to which the disclosure is by no means limited.

EXAMPLES

Exemplary Preparation: Preparation of Antibodies Specifically Bindable to SARS-CoV N Protein (1) Preparation of Antigen A full length cDNA that encodes N protein of SARS-CoV was synthesized by using a genomic RNA sequence of SARS-CoV (GenBank Accession No.: AY274119), according to a method described in Fujimoto K. et al., 2008, *J. Clin. Microbiol.*, vol. 46, p. 302-310. The obtained cDNA was integrated downstream of a sequence that encodes a His tag (6 histidine residues) of pQE30 vector (from QIAGEN), thereby obtaining a SARS-CoV NP expression vector. By using the thus obtained expression vector, a His-tagged recombinant N protein was expressed in *E. coli* according to a usual method. *E. coli* was then lysed by a usual method to obtain a soluble fraction, and the recombinant N protein was purified through a His-Trap HP column (from QIAGEN).

(2) Preparation and Screening of Hybridomas

Balb/c mice (7 weeks of age, female) were immunized with a mixture of the thus prepared recombinant N protein and complete Freund's adjuvant, and hybridomas that produce antibodies against SARS-CoV N-protein were prepared according to the method described by Kohler G. and Milstein C., *Nature*, vol. 256, pp. 495-497, 1975. From among the thus obtained hybridomas, strains that produce antibodies reactive with an antigen were selected by ELISA. The selected hybridomas were cloned by the limiting dilution method, and strains that can stably produce antibodies were further selected. In this way, two types of hybridoma that can produce antibodies specifically bindable to the N protein of SARS-CoV were obtained. These hybridomas will also be referred to as "Clone 1" and "Clone 2", hereinafter.

(3) Purification of Monoclonal Antibodies

The obtained culture supernatant (100 mL) of each hybridoma was filtered through a 0.22 μm filter to remove insoluble matters. The filtered culture supernatant was passed through a column packed with 1 mL of Protein G-Sepharose 4B (from GE Healthcare), whereby the antibody was adsorbed to the column. After removing any non-specific adsorption component from the column, the column was kept under an acidic condition to release a monoclonal antibody. The recovered monoclonal antibody was purified by dialysis against 100 times the amount of phosphate buffered saline (PBS). Hereinafter, the monoclonal antibody purified from the culture supernatant of the hybridoma of Clone 1 is also referred to as a "first antibody", and the monoclonal antibody purified from the culture supernatant of the hybridoma of Clone 2 is also referred to as a "second antibody".

(4) Analysis of Amino Acid Sequences of Antibodies

Total RNA was extracted from each of the thus obtained hybridomas, and cDNA that encodes a site including the variable regions of the heavy chain and the light chain was synthesized by the 5'-RACE method. The obtained cDNA was integrated into a plasmid vector, and the base sequences that encode the variable regions of the heavy chain and the light chain of each antibody were analyzed by sequencing. Amino acid sequences were predicted from the thus determined base sequences, and the amino acid sequences of the variable regions of the heavy chain and the light chain of each antibody were obtained on the basis of the Kabat method. The amino acid sequence of each CDR was also obtained.

The amino acid sequences of the variable regions of the heavy chain and the light chain of the first antibody were as follows.

-Heavy Chain Variable Region (SEQ ID NO: 13)
QVTLKESGPGILQPSQTLSLTCSFSGFSLSTSGTGVSWIRQPSGKGLEWL
AHIYWDDDKRYNPSLKSRLTVSKDTSGNQVFLKITSVDTADTATYYCARS
NYGYDLDYWGQGTTLTVSS -Light Chain Variable Region (SEQ ID NO: 14)

-continued

```
DIVMTQSQKFMSTSVGDRVSVTCKASQNVGTNVVWYQQKPGQSPKA
LIYSASYRYSGVPDRFTGSGSGTDFTLTISNVQSEDLAEYFCQQYNNYPL
TFGSGTKLEIKRA
```

The amino acid sequences of CDR1, CDR2, and CDR3 of the light chain and the heavy chain of the first antibody were as follows. The amino acid sequences of these CDRs are those determined based on the Kabat method.

```
CDRH1:
                                         (SEQ ID NO: 1)
TSGTGVS

CDRH2:
                                         (SEQ ID NO: 2)
HIYWDDDKRYNPSLKS

CDRH3:
                                         (SEQ ID NO: 3)
SNYGYDLDY

CDRL1:
                                         (SEQ ID NO: 4)
KASQNVGTNVV

CDRL2:
                                         (SEQ ID NO: 5)
SASYRYS

CDRL3:
                                         (SEQ ID NO: 6)
QQYNNYPLT
```

The amino acid sequences of the variable regions of the heavy chain and the light chain of the second antibody were as follows.

```
-Heavy Chain Variable Region
                                         (SEQ ID NO: 15)
EVQLVESGGGLVKPGGSLKLSCAASGFTFSDYYMYWVRQTPEKRLEW
VATISDGGSYTYYPDSVKGRFTISRDNAKNNLYLQMSSLKSDDTAKYYC
ARAADYGGYFDYWGQGTTLTVSS -Light Chain Variable Region
                                         (SEQ ID NO: 16)
DIQLTQTTSSLSASLGDRVTISCSASQGISNYLNWYQQKPDGTVKLLIY
YTSSLHSGVPSRFSGSGSGTDYSLTISNLEPEDIATYYCQQYSKLPYTFG
GGTKLEIKRA
```

The amino acid sequences of CDR1, CDR2, and CDR3 of the light chain and the heavy chain of the second antibody were as follows. The amino acid sequences of these CDRs are those determined based on the Kabat method.

```
CDRH1:
                                         (SEQ ID NO: 7)
DYYMY

CDRH2:
                                         (SEQ ID NO: 8)
TISDGGSYTYYPDSVKG

CDRH3:
                                         (SEQ ID NO: 9)
AADYGGYFDY

CDRL1:
                                         (SEQ ID NO: 10)
SASQGISN

CDRL2:
                                         (SEQ ID NO: 11)
YTSSLHS

CDRL3:
                                         (SEQ ID NO: 12)
QQYSKLPYT
```

Example 1: Immunological Measurement of N Protein of SARS-CoV-2

Reagents applicable to an automated immunoassay analyzer were prepared by using the first antibody and the second antibody obtained in Exemplary Preparation, and the N protein of SARS-CoV-2 was measured with use of these reagents.

(1) Preparation of Antigen Solution

SARS-CoV-2 Nucleocapsid-His recombinant Protein (from Sino Biological Inc.), which is a recombinant N protein of SARS-CoV-2, was used as the viral antigen. The antigen was diluted with the extraction reagent or the dilution buffer to prepare antigen solution, whose concentration of viral antigen was varied among 100 pg/mL, 1,000 pg/mL and 10,000 pg/mL. Composition of the extraction reagent was given by 0.3% NP-40 (polyoxyethylene(9) octylphenyl ether), 15 mM EDTA·2Na, 60 mM NaOH, 6 mM ACES (N-(2-acetamide)-2-aminoethanesulfonic acid), 0.22 M NaCl, and 15 mM NaN$_3$, with a pH of 7.0. Composition of the dilution buffer is given by 80 mM triethanolamine hydrochloride, 1% BSA, and 0.1% NaN$_3$, with a pH of 7.5.

(2) Preparation of Reagents

R1 reagent (capture antibody-containing reagent) was prepared by labeling the first antibody or the second antibody with biotin according to a usual method, and by dissolving it in a buffer for R1 reagent (100 mM HEPES, 150 mM NaCl, 25 mM EDTA·2Na, 2.5% casein sodium salt, 1% BSA, 0.09% NaN$_3$, 0.015% Antifoam SI, pH 7.5). Concentration of each antibody in R1 reagent was found to be 1 μg/mL. As R2 reagent (solid phase), HISCL R2 reagent (from Sysmex Corporation) that contains streptavidin-immobilized magnetic particle was used. R3 reagent (detection antibody-containing reagent) was prepared by labeling the first antibody or the second antibody with alkaline phosphatase (ALP) according to a usual method, and by dissolving it in a buffer for R3 reagent (100 mM MES, 150 mM NaCl, 1 mM MgCl$_2$, 0.1 mM ZnCl$_2$, 1% BSA, 50 mg/L scavenger ALP, 0.09% NaN$_3$, 0.015% Antifoam SI, pH 6.5). Concentration of each antibody in R3 reagent was found to be 400 ng/mL. As R4 reagent (measurement buffer), HISCL R4 reagent (from Sysmex Corporation) was used. As R5 reagent (substrate solution), HISCL R5 reagent (from Sysmex Corporation) that contains CDP-Star (registered trademark) was used. As a washing liquid for the magnetic particle, HISCL cleaning liquid (from Sysmex Corporation) was used.

(3) Measurement

Measurement was conducted on an automated immunoassay analyzer HISCL-800 (from Sysmex Corporation), with use of the aforementioned R1 to R5 reagents. The measurement was conducted first by using the first antibody as the capture antibody, and the second antibody as the detection antibody. Operational details are as follows. The antigen solution (10 μL) was added to R1 reagent (60 μL) that contains the first antibody, followed by mixing, to which R2 reagent (30 μL) was added, and again followed by mixing. The magnetic particle in the resulting mixed liquid was magnetically collected to remove the supernatant, to which HISCL washing solution (300 μL) was added to wash the magnetic particle. The supernatant was removed, and R3 reagent (60 μL) that contains the second antibody was added to the magnetic particle, followed by mixing. The magnetic particle in the resulting mixed liquid was magnetically collected to remove the supernatant, to which HISCL washing solution (300 μL) was added to wash the magnetic particle. The supernatant was removed, and R4 reagent (50 μL) and R5 reagent (100 μL) were added to the magnetic particle, followed by thorough mixing. Chemiluminescence intensity was then measured. Next, the measurement was conducted by using the second antibody as the capture antibody, and the first antibody as the detection antibody. The measurement was conducted in the same way as described above, except that R1 reagent that contains the second antibody was used in place of R1 reagent that contains the first antibody, and R3 reagent that contains the first antibody was used in place of R3 reagent that contains the second antibody. For determination of the background, the measurement was conducted in the same way as described above, except that an extraction reagent free of antigen or the dilution buffer was used in place of the antigen solution. SN ratio of the measurement was calculated from measured values of each antigen solution and the background.

(4) Results

The SN ratios of the individual measurements are summarized in Table 1. In the table, "Measurement 1" is a measurement with use of the first antibody as the capture antibody and the second antibody as the detection antibody, and "Measurement 2" is a measurement with use of the second antibody as the capture antibody and the first antibody as the detection antibody. "Antigen solution A" is an antigen solution prepared by using the dilution buffer, and "Antigen solution B" is an antigen solution prepared by using the extraction reagent.

TABLE 1

|  | Antibody for R1 reagent (Capture antibody) | Antibody for R3 reagent (Detection antibody) | Antigen solution A (pg/mL) | | | Antigen solution B (pg/mL) | | |
|---|---|---|---|---|---|---|---|---|
|  |  |  | 10,000 | 1,000 | 100 | 10,000 | 1,000 | 100 |
| Measurement 1 | First antibody | Second antibody | 106.72 | 9.58 | 0.92 | 139.85 | 14.05 | 1.37 |
| Measurement 2 | Second antibody | First antibody | 10.74 | 1.18 | 0.08 | 1.60 | 0.18 | 0.00 |

As can be understood from Table 1, the SN ratio of Measurement 1 was significantly higher than the SN ratio of Measurement 2. This proves that the first antibody is suitable as the capture antibody in the immunological measurement, and the second antibody is suitable as the detection antibody in the immunological measurement. That is, the N protein of SARS-CoV-2 in the sample was found to be successfully measured by the sandwich ELISA method, with use of the first antibody as the capture antibody and the second antibody as the detection antibody. Since Measurement 1 showed high SN ratios both in the antigen solutions A and B, so that the surfactant was found not to specially affect the measurement.

Example 2: Reactivity with N Proteins of SARS-CoV, SARS-CoV-2 and MERS-CoV

Whether the N proteins of SARS-CoV and MERS-CoV can be measured by immunological measurement with use of the first antibody and the second antibody as the capture antibody and the detection antibody, respectively, was examined. For comparison, the N protein of SARS-CoV-2 was also measured.

(1) Preparation of Antigen Solution

As viral antigens, the recombinant N protein of SARS-CoV prepared in Exemplary Preparation, the commercially available recombinant N protein of SARS-CoV-2 same as that used in Example 1, and a recombinant N protein of MERS-CoV were used. The recombinant N protein of MERS-CoV was prepared by a usual method by using a known silkworm expression system. These recombinant N proteins were diluted with the dilution buffer of Example 1, to prepare antigen solutions each containing 100 pg/mL of each viral antigen.

(2) Measurement

As the reagents, R1 reagent that contains the first antibody and R3 reagent that contains the second antibody, both prepared in Example 1; and HISCL R2 reagent, HISCL R4 reagent and HISCL R5 reagent (all from by Sysmex Corporation) were used. By using these reagents, each antigen solution was measured on HISCL-800 (Sysmex Corporation), in the same way as in Example 1. The background was measured in the same way as described above, except that the dilution buffer free of antigen was used in place of the antigen solution. Luminescence intensities (HISCL counts) of the individual measurements are summarized in Table 2.

TABLE 2

| SARS-CoV-2 | SARS-CoV | MERS-CoV | Background |
|---|---|---|---|
| 40,946 | 31,709 | 1,711 | 1,648 |

(3) Results

As can be understood from Table 2, the luminescence intensities observed in the measurement of the N proteins of SARS-CoV-2 and SARS-CoV were found to be significantly higher than the background. On the other hand, the luminescence intensity observed in the measurement of the N protein of MERS-CoV was found to be comparable to that of the background. This suggests that the first antibody and the second antibody can form the sandwich immune complex with the N proteins of SARS-CoV-2 and SARS-CoV, but do not form the sandwich immune complex with the N protein of MERS-CoV.

Example 3: Reactivity with Viral Antigens of HCoV-OC43, HCoV-NL63 and HCoV-229

Whether viral antigens of HCoV-OC43, HCoV-NL63 and HCoV-229 can be measured by the immunological measurement with use of the first antibody and the second antibody as the capture antibody and the detection antibody, respectively, was examined.

(1) Preparation of Antigen Solution

As viral antigens, employed were Coronavirus Strain: OC43 Lysate (1 mg), Coronavirus Strain: NL63 Lysate (1 mg) and Coronavirus Strain: 229E Lysate (1 mg), which are inactivated solutions of HCoV-OC43, HCoV-NL63 and HCoV-229E (all from ZeptoMetrix, LLC), respectively. These inactivated solutions had been prepared by lysing the individual purified viruses in a solution that contains a surfactant, and by inactivating the viruses under heating, with a protein content of 1 mg. Each of these inactivation solutions was diluted with the dilution buffer of Example 1 to prepare antigen solutions whose protein concentration was varied among 10 ng/mL, 100 ng/mL and 1,000 ng/mL.

(2) Measurement

Each antigen solution was measured in the same way as in Example 1 on HISCL-800 (from Sysmex Corporation) with use of R1 to R5 reagents same as those in Example 2. The background was measured in the same way as described above, except that the dilution buffer free of antigen was used in place of the antigen solution. Luminescence intensities (HISCL counts) of the individual measurements are summarized in Table 3.

TABLE 3

| OC43 (pg/mL) | | | NL63 (pg/mL) | | | 229E (pg/mL) | | | Back-ground |
|---|---|---|---|---|---|---|---|---|---|
| 1,000 | 100 | 10 | 1,000 | 100 | 10 | 1,000 | 100 | 10 | |
| 584 | 521 | 497 | 532 | 569 | 522 | 583 | 564 | 536 | 524 |

(3) Results

As can be understood from Table 3, the luminescence intensities observed in the measurement of the proteins contained in the inactivated solutions of HCoV-OC43, HCoV-NL63 and HCoV-229E were found to be comparable to that of the background. This suggests that the first antibody and the second antibody do not form the sandwich immune complex with any of viral antigens of HCoV-OC43, HCoV-NL63 and HCoV-229E.

Example 4: Examination of Limit of Detection

Limit of detection of the immunological measurement with use of the first antibody and the second antibody as the capture antibody and the detection antibody, respectively, was examined by using an antigen solution that contains a low concentration of N protein of SARS-CoV-2.

(1) Preparation of Antigen Solution

SARS-CoV-2 Nucleocapsid-His recombinant Protein (from Sino Biological Inc.) was used as the viral antigen. The antigen was added to a calibrator dilution buffer or the extraction reagent of Example 1 to prepare an antigen solution that contains the viral antigen whose concentration varied among 1 pg/mL, 2 pg/mL, 3 pg/mL, 4 pg/mL, 5 pg/mL and 10 pg/mL. Ten aliquots (n=10) of the antigen solution were prepared for each concentration. The calibrator dilution buffer means a buffer free of surfactant, and is used for diluting any standard substance solution for preparing an analytical curve. Composition of the calibrator dilution buffer was given by 80 mM triethanolamine hydrochloride, 1% BSA and 0.1% $NaN_3$, with a pH of 7.5.

(2) Measurement

Figure 2A:
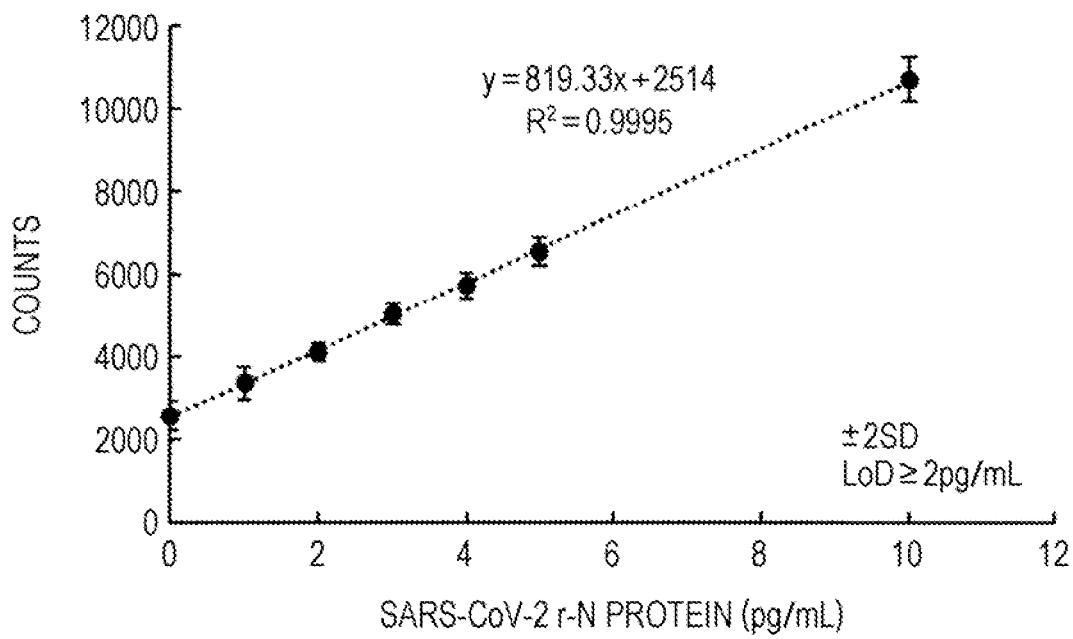
FIG. 2A is a graph plotting averaged luminescence intensity versus antigen concentration, obtained when a sample that contains a viral antigen in an extraction reagent was measured by the measurement method of this embodiment.
Figure 2B:
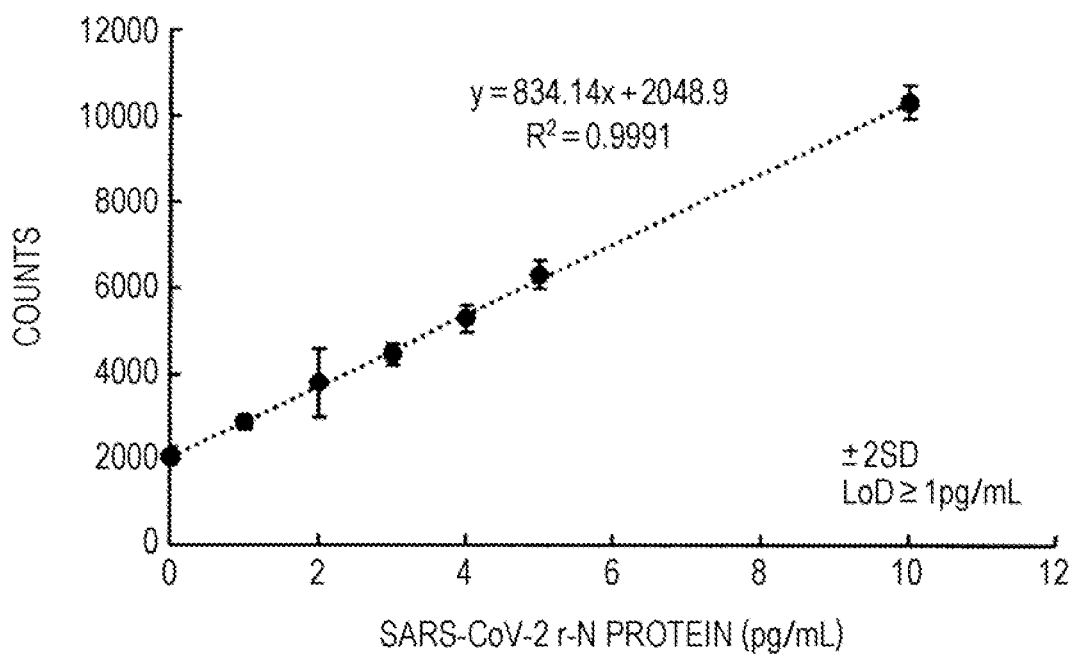
FIG. 2B is a graph plotting averaged luminescence intensity versus antigen concentration, obtained when a sample that contains a viral antigen in a dilution buffer was measured by the measurement method of this embodiment.

Each antigen solution was measured in the same way as in Example 1 on HISCL-800 (from Sysmex Corporation) with use of R1 to R5 reagents same as those in Example 2. The background was measured in the same way as described above, except that the calibrator dilution buffer free of antigen or the extraction reagent was used in place of the antigen solution. Average value (Av), standard deviation (SD) and coefficient of variation (CV) of luminescence intensity (HISCL counts) of each antigen solution are summarized in Table 4. In the Table, "Antigen solution C" is an antigen solution prepared by using the calibrator dilution buffer, and the "Antigen solution D" is an antigen solution prepared by using the extraction reagent. Graphs that plot the averaged luminescence intensity versus antigen concentration are illustrated in FIGS. 2A and 2B.

TABLE 4

| Antigen concentration | Antigen solution C | | | Antigen solution D | | |
|---|---|---|---|---|---|---|
| pg/mL | Av | SD | CV | Av | SD | CV |
| 0 | 2069.1 | 100.6 | 4.9 | 2561.6 | 168.1 | 6.6 |
| 1 | 2864.6 | 78.3 | 2.7 | 3350.7 | 194.9 | 5.8 |
| 2 | 3801.0 | 399.0 | 10.5 | 4106.6 | 115.2 | 2.8 |
| 3 | 4457.9 | 126.6 | 2.8 | 5041.2 | 128.1 | 2.5 |
| 4 | 5283.8 | 159.4 | 3.0 | 5718.1 | 155.7 | 2.7 |
| 5 | 6331.4 | 164.6 | 2.6 | 6548.6 | 172.3 | 2.6 |
| 10 | 10388.3 | 187.9 | 1.8 | 10754.3 | 272.3 | 2.5 |

(3) Results

As can be understood from FIGS. 2A and 2B, signals corresponded to the antigen concentration were detected even from the samples that contain the N protein of SARS-CoV-2, whose concentration was as low as 10 pg/mL or below. As seen in Table 4, the limit of detection (LoD) was found to be 1 pg/mL or above for the antigen solution prepared by using the calibrator dilution buffer, and LoD was found to be 2 pg/mL or above for the antigen solution prepared by using the extraction reagent.

Example 5: Correlation Between Immunological Measurement and PCR Method

A commercially available biological sample that contains SARS-CoV-2 was measured by the measurement method of this embodiment and the PCR method, and the measured values obtained by both methods were compared to examine whether any correlation is found between the measurement method of this embodiment and the PCR method.

(1) Pretreatment of Biological Sample

Nasopharyngeal swab specimens (36 specimens) from SARS-CoV-2 infected patients were purchased from Cantor Bioconnect, Inc. Each specimen (500 µL) and the extraction reagent (500 µL) of Example 1 were mixed to prepare an antigen solution. The obtained antigen solution was used for immunological measurement. RNA was extracted from each of the aforementioned specimens, by using QIAamp Viral RNA Mini kit (from QIAGEN). The obtained RNA solution was used for measurement by PCR method.

(2) Immunological Measurement

The antigen solution was measured in the same way as in Example 1 on HISCL-800 (from Sysmex Corporation) with use of R1 to R5 reagents same as those in Example 2. The background was measured in the same way as described above, except that the calibrator dilution buffer free of antigen was used in place of the antigen solution.

(3) Measurement by PCR Method

Measurement by the PCR method was conducted according to the procedures of "detection of 2019-nCoV by a real time one-step RT-PCR method using the TaqMan Probe", described in "Manual for the Detection of Pathogen 2019-nCoV Ver. 2.9.1" (Mar. 19, 2020), issued by National Institute of Infectious Diseases. QuantiTect (registered trademark) Probe RT-PCR kit (from QIAGEN) was used as the real-time RT-PCR reagent. The amplification was conducted under the conditions described in the manual attached to the kit. The sequences of the primer set and the probe used for real-time RT-PCR were as follows. Hereinbelow, "FAM" represents fluorescent dye (fluorescein amidite), and "BHQ" represents black hole quencher.

```
Forward:
                                        (SEQ ID NO: 17)
5'-CACATTGGCACCCGCAATC-3'

Reverse:
                                        (SEQ ID NO: 18)
5'-GAGGAACGAGAAGAGGCTTG-3'

Probe:
                                        (SEQ ID NO: 19)
5'-FAM-ACTTCCTCAAGGAACAACATTGCCA-BHQ-3'
```

(4) Results

Figure 3:
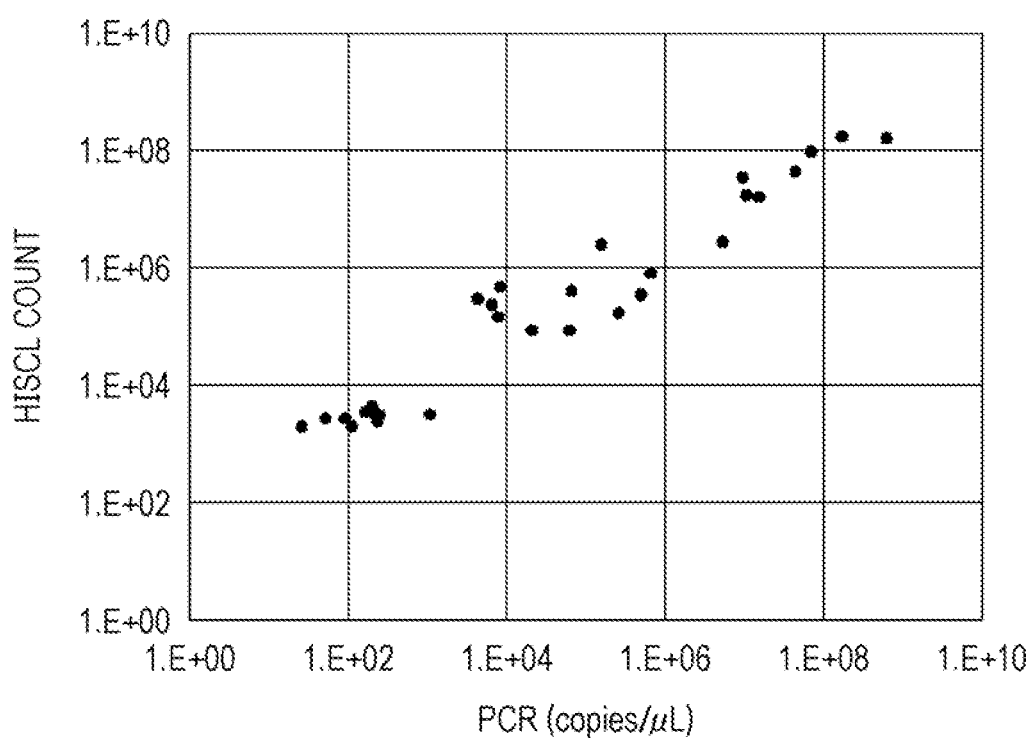
FIG. 3 is a graph plotting measured values of a sample collected from patients infected with SARS-CoV-2, obtained both by the measurement method of this embodiment and by the PCR method.

Measured values for the individual specimens obtained by the measurement method of this embodiment and the PCR method were plotted on X-Y plane, having luminescence intensity (HISCL counts) scaled on Y-axis, and the viral RNA concentration (copies/μL) scaled on X-axis. The obtained graph is illustrated in FIG. 3. As suggested by FIG. 3, correlation between the measurement method of this embodiment and the PCR method was observed.

What is claimed is:

1. A method for measuring a nucleoprotein of severe acute respiratory syndrome coronavirus (SARS-COV) or SARS-COV-2 in a sample by using a capture antibody and a detection antibody, the method comprising
forming a sandwich immune complex that contains the capture antibody, the nucleoprotein of SARS-COV or SARS-COV-2 and the detection antibody,
the capture antibody comprising a heavy chain variable region that comprises complementary determining region 1 (CDR1) comprising the amino acid sequence of SEQ ID NO: 1, CDR2 comprising the amino acid sequence of SEQ ID NO: 2 and CDR3 comprising the amino acid sequence of SEQ ID NO: 3, and a light chain variable region that comprises CDR1 comprising the amino acid sequence of SEQ ID NO: 4, CDR2 comprising the amino acid sequence of SEQ ID NO: 5 and CDR3 comprising the amino acid sequence of SEQ ID NO: 6, and
the detection antibody comprising a heavy chain variable region that comprises CDR1 comprising the amino acid sequence of SEQ ID NO: 7, CDR2 comprising the amino acid sequence of SEQ ID NO: 8 and CDR3 comprising the amino acid sequence of SEQ ID NO: 9, and a light chain variable region that comprises CDR1 comprising the amino acid sequence of SEQ ID NO: 10, CDR2 comprising the amino acid sequence of SEQ ID NO: 11 and CDR3 comprising the amino acid sequence of SEQ ID NO:12,
wherein the CDRs of the capture antibody and the detection antibody are determined based on the Kabat method.

2. The method according to claim 1, wherein the capture antibody and the detection antibody do not form the sandwich immune complex with a nucleoprotein of Middle East respiratory syndrome coronavirus (MERS-CoV), and viral antigens of human coronavirus OC43 (HCoV-OC43), HCoV-NL63, or HCoV-229.

3. The method according to claim 1, wherein the capture antibody comprises the heavy chain variable region comprising the amino acid sequence of SEQ ID NO: 13, and the light chain variable region comprising the amino acid sequence of SEQ ID NO: 14, and
the detection antibody comprises the heavy chain variable region comprising the amino acid sequence of SEQ ID NO: 15, and the light chain variable region comprising the amino acid sequence of SEQ ID NO: 16.

4. The method according to claim 1, wherein the capture antibody type is immunoglobulin G (IgG), reduced IgG, Fab, Fab', F(ab')2, Fv, scFv, a diabody or a triabody.

5. The method according to claim 1, wherein the detection antibody type is IgG, reduced IgG, Fab, Fab', F(ab')2, Fv, scFv, a diabody or a triabody.

6. The method according to claim 1, wherein the sample is a biological sample.

7. The method according to claim 1, wherein the capture antibody is immobilized on a solid phase.

8. The method according to claim 7, wherein the solid phase is a magnetic particle or a microplate.

9. The method according to claim 1, wherein the detection antibody is labeled with a labeling substance.

10. The method according to claim 9, wherein the labeling substance is at least one enzyme selected from the group consisting of alkaline phosphatase, peroxidase, P-galactosidase, glucosidase, polyphenol oxidase, tyrosinase, acid phosphatase and luciferase.

11. An antibody set for measuring a nucleoprotein of severe acute respiratory syndrome coronavirus (SARS-COV) or SARS-COV-2 in a sample by an immunological measurement method,
the antibody set comprising a capture antibody and a detection antibody that form a sandwich immune complex with the nucleoprotein of SARS-COV or SARS-COV-2 in the immunological measurement method, the capture antibody comprising a heavy chain variable region that comprises CDR1 comprising the amino acid sequence of SEQ ID NO: 1, CDR2 comprising the amino acid sequence of SEQ ID NO: 2 and CDR3 comprising the amino acid sequence of SEQ ID NO: 3; and a light chain variable region that comprises CDR1 comprising the amino acid sequence of SEQ ID NO: 4, CDR2 comprising the amino acid sequence of SEQ ID NO: 5 and CDR3 comprising the amino acid sequence of SEQ ID NO: 6, and
the detection antibody comprising a heavy chain variable region that comprises CDR1 comprising the amino acid sequence of SEQ ID NO: 7, CDR2 comprising the amino acid sequence of SEQ ID NO: 8 and CDR3 comprising the amino acid sequence of SEQ K NO: 9; and a light chain variable region that comprises CDR1 comprising the amino acid sequence of SEQ ID NO: 10, CDR2 comprising the amino sequence of SEQ ID NO: 11 and CDR3 comprising the amino acid sequence of SEQ ID NO: 12,
wherein the CDRs of the capture antibody and the detection antibody are determined based on the Kabat method.

12. A reagent kit comprising the capture antibody and the detection antibody described in claim 11.

13. The reagent kit according to claim 12, comprising a first reagent and a second reagent, the first reagent comprising the capture antibody and the second reagent comprising the detection antibody.

14. The reagent kit according to claim 12, wherein the capture antibody is immobilized on a solid phase.

15. The reagent kit according to claim 14, wherein the solid phase is a magnetic particle or a microplate.

16. The reagent kit according to claim 12, wherein the detection antibody is labeled with a labeling substance.

17. The reagent kit according to claim 16, wherein the labeling substance is at least one enzyme selected from the group consisting of alkaline phosphatase, peroxidase, P-galactosidase, glucosidase, polyphenol oxidase, tyrosinase, acid phosphatase and luciferase.

18. The reagent kit according to claim 17, further comprising a substrate for the enzyme.

* * * * *